United States Patent [19]
Gelfgat et al.

[11] Patent Number: 5,746,702
[45] Date of Patent: May 5, 1998

[54] METHOD OF AND DEVICE FOR LOCAL SKIN MASSAGING

[75] Inventors: David Mendeloevich Gelfgat, Dakabrietov; Sergei Yakovlevich Skipidarov, Moldayakaya, both of Russian Federation; Michael Yakhats, Los Angeles, Calif.; Vyacheslav Tikhonovich Kamensky, Sovataki, Russian Federation

[73] Assignee: A. Relin, Langhorne, Pa.

[21] Appl. No.: 564,138

[22] PCT Filed: Mar. 31, 1994

[86] PCT No.: PCT/RU94/00065

§ 371 Date: Nov. 24, 1995

§ 102(e) Date: Nov. 24, 1995

[87] PCT Pub. No.: WO94/27532

PCT Pub. Date: Dec. 8, 1994

[30] Foreign Application Priority Data

May 27, 1993 [RU] Russian Federation ............ 93031379

[51] Int. Cl.$^6$ .................................................... A61H 15/02
[52] U.S. Cl. .................... 601/15; 601/132; 601/133
[58] Field of Search ................ 601/15, 48, 131–138, 601/143, 118, 122, 125

[56] References Cited

U.S. PATENT DOCUMENTS

| | | | |
|---|---|---|---|
| 737,473 | 8/1903 | Porter | 606/204 |
| 3,168,895 | 2/1965 | Okuhara | 601/15 X |
| 4,082,089 | 4/1978 | Moriyama et al. | 601/19 |
| 4,614,191 | 9/1986 | Perler | 601/15 X |
| 5,327,886 | 7/1994 | Chiu | 601/15 X |
| 5,617,868 | 4/1997 | Harada et al. | 128/748 X |

FOREIGN PATENT DOCUMENTS

| | | | |
|---|---|---|---|
| 406245949 | 9/1994 | Japan | 601/15 |
| 8100202 | 2/1981 | WIPO | 606/204 |

*Primary Examiner*—Danton D. DeMille
*Attorney, Agent, or Firm*—Ilya Zborovsky

[57] ABSTRACT

The invention relates to medical technology, specifically to devices for local massage of the skin, especially facial skin. The purpose of the invention is to improve the effectiveness of the massage while making the device more ergonomic. The device comprises identical massaging heads (1, 2), each of which consists of the following: heating elements which are in contact with a thermal contact plate (8); a heat dissipation system (9) designed, for example, in the form of an air radiator; a housing (10) with a convex spherical surface (11) and a holder made up of the plates (12, 13) with an aperture (14) whose wall has a spherical concave surface, the aperture forming an articulated joint with the surface (11) and thereby ensuring close contact throughout the massage session between the thermal contact plate (8) and the area being massaged. The device is provided with an automatic contrasting thermocycling unit consisting of a voltage stabilizer (34) and a pulse generator (35) connected in series, the switching component (33) being connected between the direct current source (32) and the heating elements in the massaging heads (1, 2). During the massage, the thermal contact plate (8) in contact with the massaged area is periodically cooled and heated by changing the direction of current passing through the heating elements. The clamp units are designed preferably in the form of a headpiece consisting of arched spring units (22, 23) whose end sections fit into slots (20) in the holder, thereby allowing the massaging heads (1, 2) to be moved along the clamp units.

13 Claims, 3 Drawing Sheets

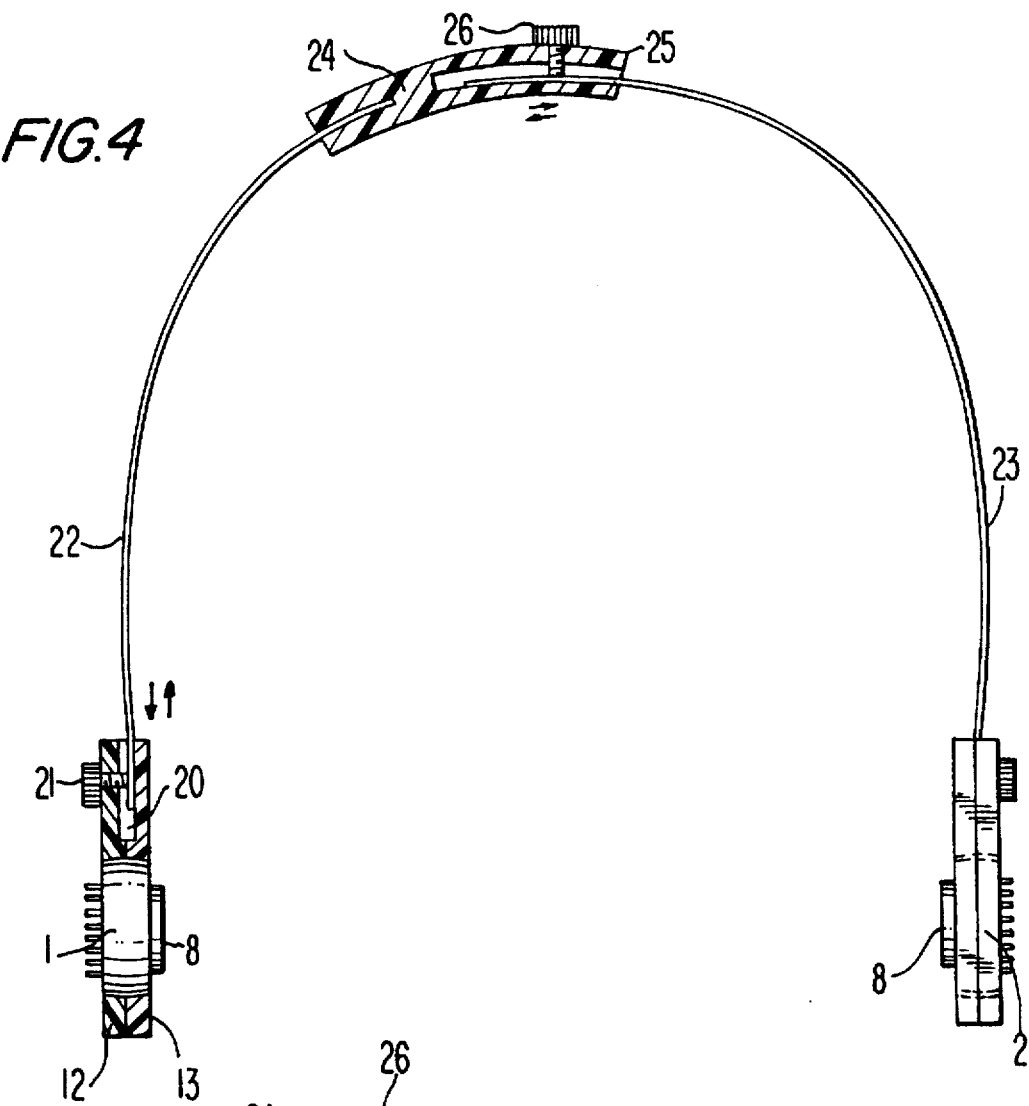
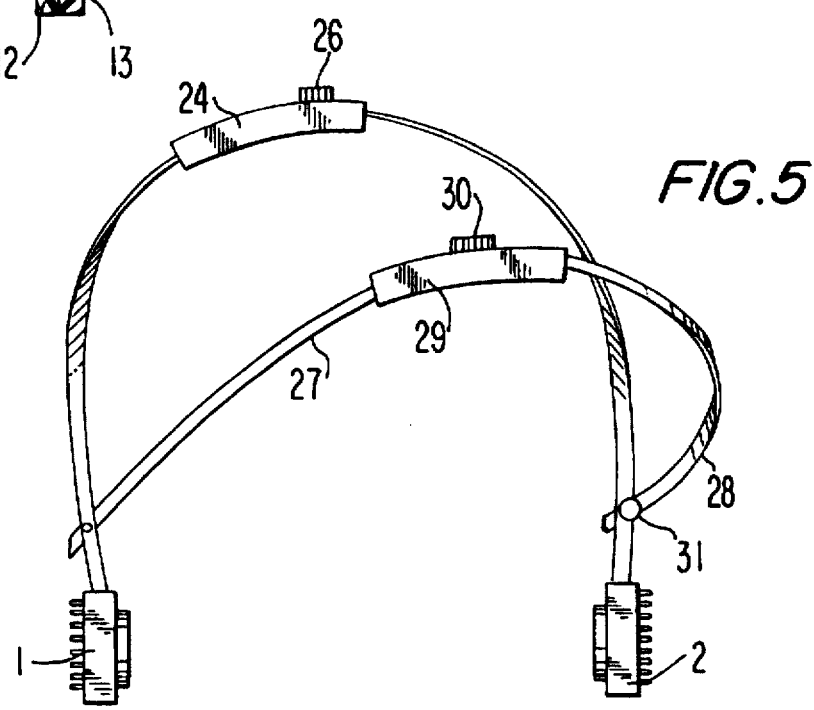

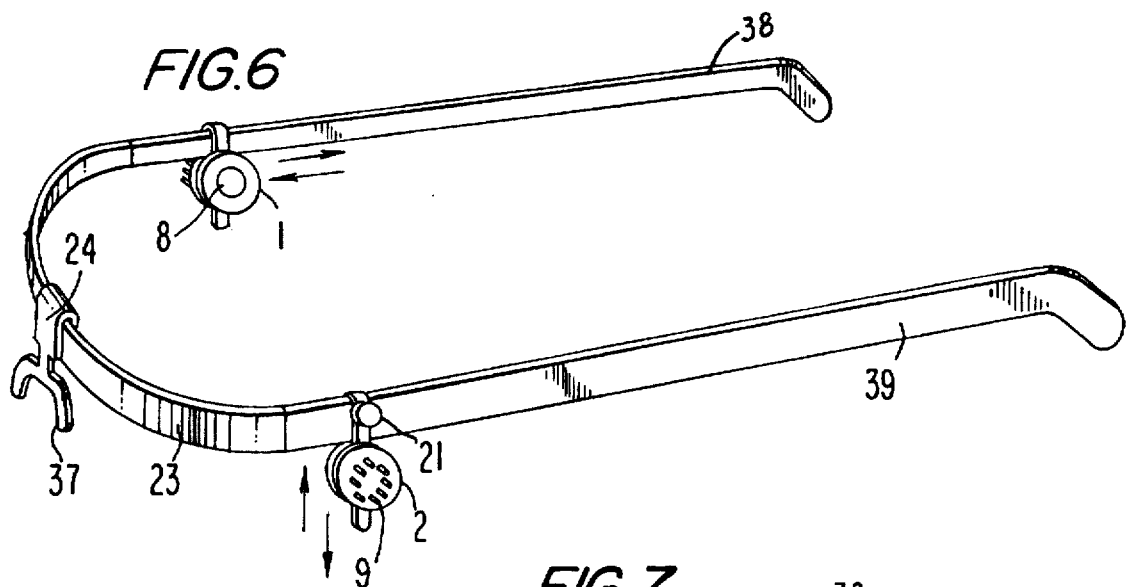
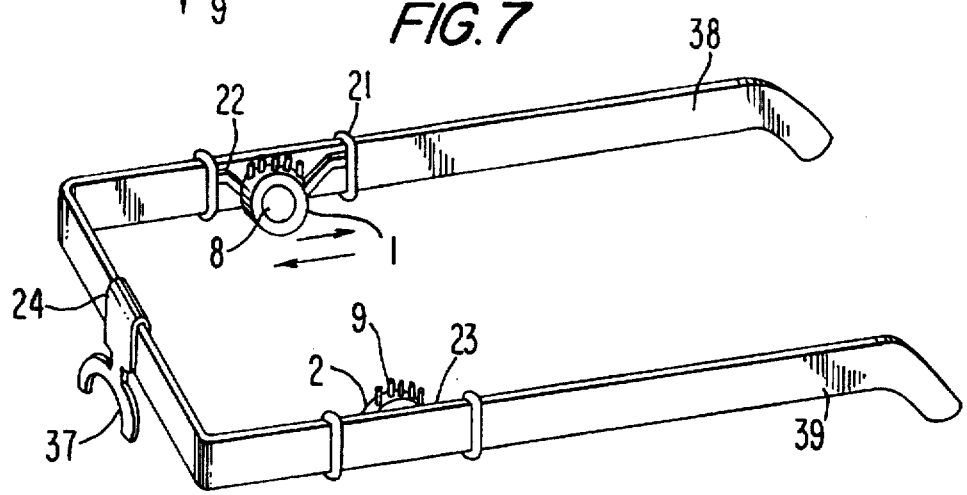
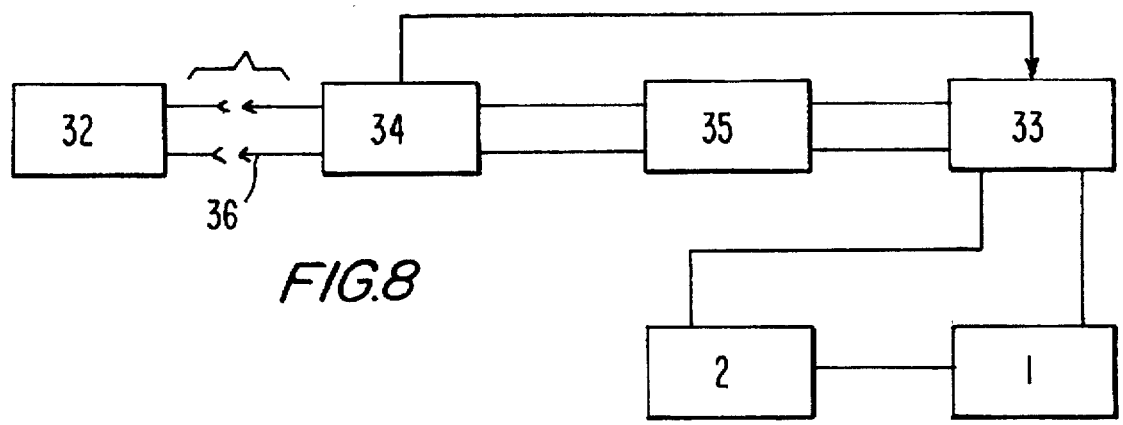

METHOD OF AND DEVICE FOR LOCAL SKIN MASSAGING

BACKGROUND OF THE INVENTION

The invention relates to a medical field and can be used in devices for local skin massage, which are used preferably during perfolactic and stimulating massage of facial skin for cosmetic purpose.

More particularly, the present invention relates to a method of and device for local massaging of skin.

The device for local massage preferably of facial skin is known, which includes a cylindrical casing with a conical end provided with heat contact plate, and thermal element adjoining the plate and connected with a block for regulation of temperature of the plate, as well as a system of heat withdrawal (see French patent No. 2,177,818, Class P 25 B 21/02, 1974). In this known device, before the beginning of massage the regulator sets the required temperature of the heat contact plate, and massage of local portion of the facial skin is performed manually.

The disadvantage of the known device is a low efficiency of the massage, which results from difficulty of maintaining a reliable contact of the heat contact plate with skin, and necessity of periodical switching by the massager of a temperature regulator.

Another device for contrast temperature action on local skin portions with performing of local massage is known, which includes thermal elements adjoining the heat contact plate and a system of heat withdrawal, accommodated in a casing, a source of direct current connected through a commutating element to the thermal elements, and elements for clamping the device on a human body (see Swiss patent No. 527,506, Class HO1V1/00, 1972). In this known device the clamping elements can be formed for example as a watch bracelet made of an elastic material so that the pressing of the heat contact plate to the skin portion to be massaged is provided.

The disadvantage of this known device is low efficiency of massaging since during setting of the device it is not possible to provide a reliable heat contact of the heat contact plate with the portion to be massaged during the fixed position of the plate. The air gaps which are produced lead to formation of thermal resistance, which in turn leads to a non-isothermicity of the surface to be massaged, and the efficiency of the massage is reduced.

A device for local skin massage which is the closest in its technical aspects to the device of the present invention has a casing, in which a heat contact plate is mounted, a commutating element, and means for cooling and heating of the heat contact plate which include a source of the direct current connected through the commutating element to the thermal elements adjoining the heat contact plate, and a system of heat withdrawal (see French patent No. 2,244,145, Class 861 AGIH7/00, 1975). This known device is used predominantly for massaging facial skin, and transition from heating mode to cooling mode is performed by switching of the commutating element of the massager.

The disadvantage of this known device is low efficiency of massaging since it is difficult to produce constant reliable pressing of the heat contact plate to the portion to be massaged. In the known device during a long-term massage (tens of minutes) the hand of a massaging person, uses, and the tight abutment of the heat contact plate against the skin deteriorates. In addition, the known device has low ergonomic properties since in order to change the mode it is necessary to manually switch of the commutating element after exactly fixed time intervals, which is tiring.

SUMMARY OF THE INVENTION

The invention is designed for increasing the efficiency of massaging of local skin portions with simultaneous improvement of ergonomic properties.

In order to achieve this technical result, in the device for local skin massaging which includes a casing with a heat contact plate mounted on it, a commutating element, and means for cooling and heating of the heat contact plate including a source of direct current connected through the commutating element to the thermal elements adjoining the heat contact plate, and a system of heat withdrawal, there are additionally introduced a block of contrast thermocycling, a holder with an opening for the casing, and elements of pressing the heat contact plate to the skin which adjoin the holder, and the block of automatic contrast thermocycling is introduced into a space between the source of direct and the commutating element, the opening of the holder has a spherical concave wall, the casing is formed with a spherical convex wall which forms with the opening a hinge connection, and the holder is arranged with the possibility of displacing along the elements of pressing, and preferably: the block of automatic contrast thermocycling is formed as a voltage stabilizer and power generator connected in series with the input of the voltage stabilizer connected to the output of the source of direct current and the output of the pulse generator connected to the commutating element; the heat withdrawal system is formed with a convex spherical surface so that its contact connection with the spherical concave surface of the opening of the holder is hinge-like; an additional casing is provided in the device and accommodates the block of automatic contrast thermocycling and the source of the direct current, with an additional casing of handles of the regulator of the mode of contrast thermocycling arranged on the front panel, and the additional casing is connected with the holder by thread-like elements, the device is formed as two identical massage blocks each containing the heat contact plate arranged on the casing, thermal elements adjoining the heat contact plate, the holder with the opening and having the contact connection with the casing which is hinge-shaped, and the system of heat withdrawal, with the blocks connected with one another through the pressing elements; the pressing elements are formed as two identical parts with their connection formed so as to allow change of relative location of the massaging blocks; the pressing elements are formed as a head of arcuate springs with the end portions arranged in gaps of the holders, and an arcuate fixator with an arcuate spring is arranged in the central zone of the head and accommodates the end of the arcuate spring; or the pressing elements are formed as spectacle frame curves connected by an arcuate spring with a support element connected to the center of the springs, and the massaging blocks are arranged on the curves so as to move in two mutually perpendicular directions, or the pressing elements are formed as a part of a spectacle frame with an elastic element arranged on each curve, and massaging block fixed on the elastic element, so that the elastic element is formed so as to be movable along the curve.

Since the holder with the opening forming a hinge connection with the casing is introduced in the device, it allows a reliable heat contact of the whole surface of the heat contact plate with the skin portion to be massaged even when the orientation of the holder is changed. Thereby, the generation of parasitic air gap between the skin and heat contact plate is eliminated and a uniform heat action along the while surface of the skin portion to be massaged is provided during the whole time of massaging, so that efficiency of the massaging is increased. Various structures can be used for the hinge connection, however, it is preferable when the casing is formed with the convex spherical surface which is used as one element of a hinge connection, while the holder is formed with an opening having a concave spherical wall used as a second element of the hinge connection, and therefore the construction is substantially simplified and the operational reliability is increased due to extended surface of the hinge connection. The outer surface of the system of heat withdrawal which adjoins the concave spherical surface of the opening of the holder can be also formed with a spherical outer surface to be one of the elements of the hinge connection, which provides simplification of the construction. In order to increase the efficiency of massaging due to contrast thermocycling of the portion to be massaged by successive heating and cooling performed through exactly fixed time intervals, with simultaneous improvement of the ergonomic properties due to facilitation of operational conditions of a massaging personnel, the device is provided with a block of automatic contrast thermocycling which is introduced between the commutating element and the source of direct current. Preferably, the block of automatic contrast thermocycling is formed as a voltage stabilizer and power generator connected in series, with the input of the voltage stabilizer connected to the output of the source of direct current and the output of the pulse generator connected to the commutating element, which provides the possibility of free regulation of a mode of the process of thermocycling with simultaneous simplification of the block construction. In order to increase the efficiency of the massaging process due to efficient change of the mode of the contrast thermocycling, preferably the block of automatic contrast thermocycling is arranged in an additional casing with the handles of mode regulators, for example, handles of a potentiometer block, arranged on the front panel of the additional casing. Here the additional casing is fixed to the holder by thread-like elements, therefore it can be located on a patient's chest so as to increase the convenience of device operation, to improve ergonomic properties. Since the claimed device is provided preferably for massage of facial skin, it is preferable to form it of two identical massage blocks and to arrange them during massaging at both sides of the plane extending through the face center. The massage blocks are connected by pressing elements which are formed of two identical parts with the possibility of changing of mutual location of the massage blocks and the efficient change of the mutual location of the massage blocks is provided in dependence on the patient's face size, and at the same time the efficiency of massage is increased because of the reliable pressing of the heat contact plates against the face skin. The pressing elements can have different constructions, however, it is preferable to form pressing elements as a head of arcuate springs with their end portions located in slots of holders, so that the construction of the pressing elements is simplified to the maximum and it is possible to displace the holders along the springs. In order to extent the range of distances between the massaging blocks, an arcuate fixator with a curved path can be arranged in a central zone of the head, and the end of the arcuate spring can be arranged in the slot. Depending on the size of the patient's face, the spring is displaced in the curved path, and the distance between the massage blocks is regulated, with simultaneous reliable heat contact with the skin. The pressing elements can be formed as spectacle frame arcs connected by an arcuate spring with a support element fixed to a spring center, and the massage blocks are arranged so as to displace in mutually perpendicular directions, so that the range of facial skin portions which can be massaged is expanded due to the possibility of movement of the massage blocks in two mutually perpendicular directions. The pressing elements can be formed also as a part of a spectacle frame, and an elastic element which mounts the massage block is located on each arc, and the elastic element is formed so that it can displace along the spectacle arc, to provide a possibility of arranging the massage block in the most favorable massage zones.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The attached drawings illustrate:

FIG. 4 is a general view of the device (transverse cross-section—front view) with pressing elements in the form of a head;

FIG. 5 is a general view of the device (in isometric projection) with two arcuate springs;

FIG. 6 is a general view of the device (in isometric projection) with pressing elements formed as spectacle arcs connected by an arcuate spring;

FIG. 7 is a general view of the device (in isometric projection) with pressing elements formed as a part of a spectacle frame;

FIG. 8 is a block diagram of a block of contrast thermocycling.

DESCRIPTION OF PREFERRED EMBODIMENTS

Figure 2:
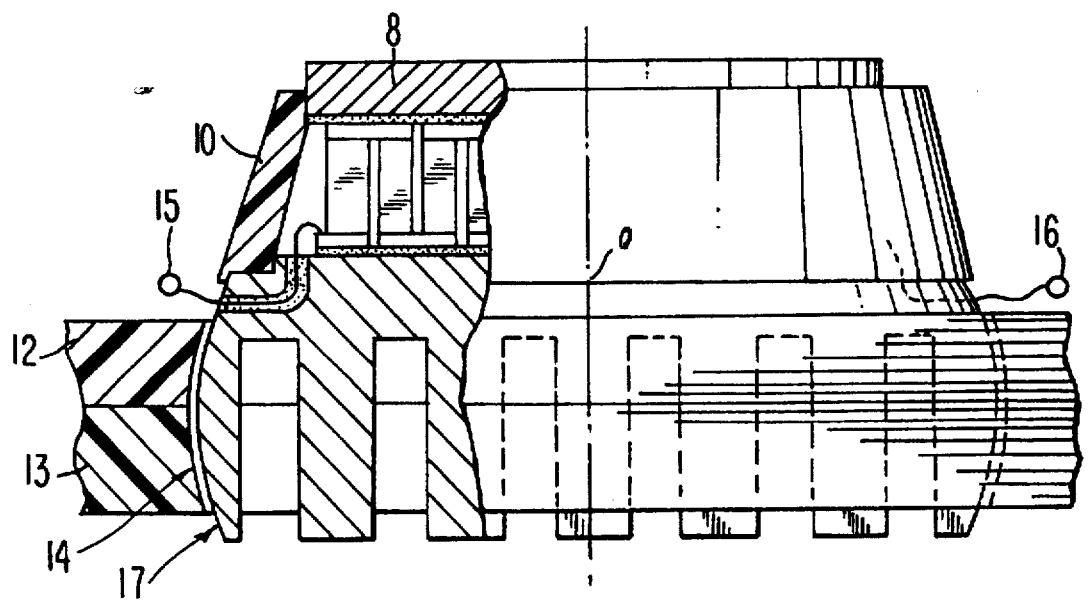
FIG. 2 is a massage block (transverse cross-section) with a hinge connection formed by a system of heat withdrawal.
Figure 3:
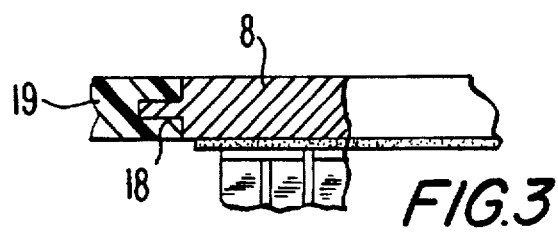
FIG. 3 is a heat contact plate with a springy support element.

A claimed device for local massage of skin includes: massaging blocks 1, 2 each including thermal elements composed of semi-conductor branches of electronic conductivity ("n"type) 3, semiconductor branches of whole conductivity ("p"type) 4, connected by commutating webs 5, electro-isolating layer 6, 7, a heat contact plate 8, a system of heat withdrawal 9 formed for example as an air radiator, a casing 10 which can be formed with a spherical convex wall 11, a holder composed of two parts 12, 13 having an opening with a spherical concave wall 14, and electrical terminals 15, 16; the system of heat withdrawal can be formed with a spherical outer wall 17 (see FIG. 2); the heat contact element 8 can be formed with a projection along its perimeter 18, on which a support element 19 can be fixed (see FIG. 3); a slot 20 can be formed in the holder, and ends of arcuate springs 22, 23 which form a head can be fixed in the slot by fixing elements 21; an arcuate fixator 24 is arranged in the center zone of the head and has a curved path 25 so that the end of the arcuate spring is fixed in the curved path by a fixing element 26; a system of additional arcuate spring 27, 28 which are identical to the main springs, with an arcuate fixator 29, a fixing element 30 and an additional fixing element 31 (see FIG. 5) can be provided; a source of direct current 32 connected through a commutating element 33 to thermal elements of the massage blocks; a voltage stabilizer 34 and a pulse generator 35 connected in series so that the input of the voltage stabilizer is connected to the source of direct current through an plug connection 36; when the pressing elements are formed as a part of spectacle frames, a support element 37 and arcs of a spectacle frame 38, 39 are utilized (see FIGS. 6, 7).

Figure 1:
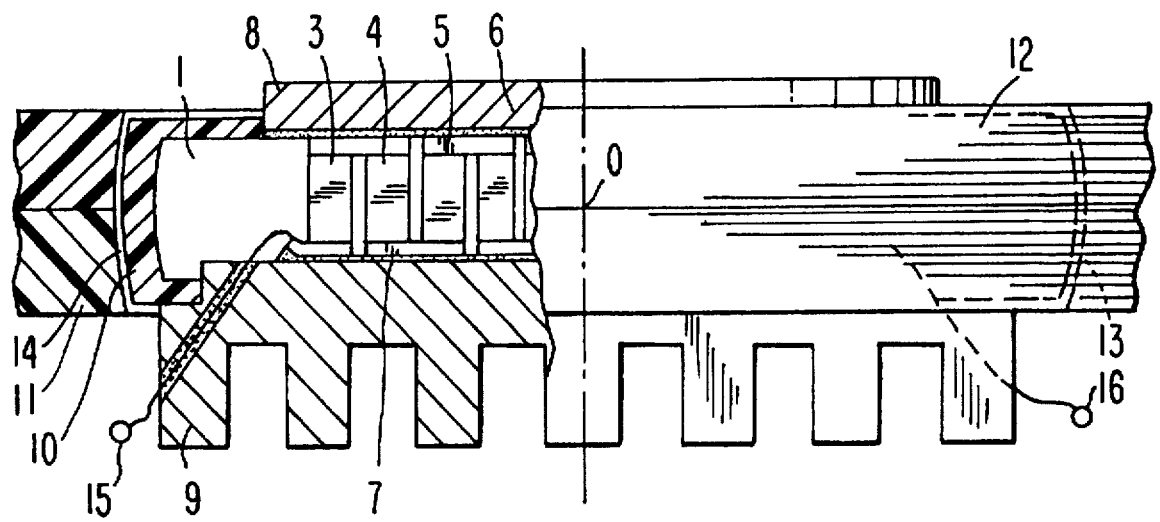
FIG. 1 is a massage block (transverse cross-section) with a hinge connection formed by a casing.

The branches of the thermal elements 3, 4 are preferably composed of highly efficient semiconductor materials, for example from a ternary alloy based on bismuth tolaride. The heat contact plate 8 is composed of materials which have high thermal conductivity, for example copper, aluminum oxide ceramics, aluminum nitrite, etc., and when electro-isolating material is utilized, commutating webs 5 of the thermal elements are connected directly to the heat contact plate 8. A thin layer (with thickness less than 0.1 mm) of the protective biological coating (not shown in the drawing) can be applied on the outer surface of the heat contact plate 8. The casing 10 is preferably composed of a heat insulating material, for example of plastic. An outer wall of the casing is formed with a convex spherical surface 11, and the center of this sphere 0 (see FIG. 1) is located in a geometrical center of the casing. The holder which is used for mounting of the casing 10 on the pressing elements is preferably formed composite, for example composed of two parts 12, 13 which are connected with one another by catches and fixing elements (not shown in the drawings), which substantially simplifies the assembly process for the device. An opening having a concave spherical wall 14 is formed in the holder and has a curvature which corresponds to the curvature of the wall of the casing 11, so that during connection of the contacting walls 11, 14 a hinge connection is formed. The heat contact plate 8 preferably is formed along its perimeter with a projection 18 which is fixed in the support element 11 composed of a spring material for example rubber (see FIG. 3), which contributes to improvement of heat contact with skin. The system of heat withdrawal 9 is preferably formed as an air radiator (see FIGS. 1–7). The outer surface of the system of heat withdrawal can be formed with convex and spherical surface 17 (see FIG. 2), and its contact with the concave spherical surface of the holder 14 forms a hinge connection. The pressing elements which provide pressing of the heat contact plates 8 to the skin portions to be massaged can be formed for example as a head of arcuate springs 22, 23, whose ends are fixed in slots of the holders 20 (see FIGS. 4, 5); or as a part of a spectacle frame in which the curves of the spectacle 38, 39 are connected by arcuate springs 22, 23 (see FIG. 6); or as a part of a spectacle frame in which elastic elements mounting the massage blocks 1, 2 are arranged on the curves of the spectacle 38, 39 (see FIG. 7). When the pressing elements are formed as the head of a system of the arcuate spring 22, 23, identical elements 27, 28 (see FIG. 5) can be introduced to increase the reliability of fixation of the massage blocks 1, 2 on the skin portions to be massaged. Accumulators, galvanic elements, photoelectric batteries, alternating current rectifiers connected to a network and other sources can be used as sources of direct current 32 which provide energy supply to the thermal elements of the massage blocks 1, 2. The voltage stabilizer 34 can be composed of standard elements, for example of a transistor connected in series to the stabilizer, with a circuit including a capacitor and potentiometer connected parallel to them. The pulse generator 35 which is used for automatic supply of bipolar current pulses to the thermal elements is formed as a conventional generator of infralow frequencies (pulse length 60–90 S), and composed of standard units and parts. For example the pulse generator 35 can be composed of two field transistors connected in series to one another and connected to a transistor, potentiometers, capacitors and an electronic relay with a diode connected parallel to it, with the commutating element 33 formed as a contact group of an electronic relay, connecting the output of the pulse generators 35 with the thermal elements of massage blocks 1, 2 (see FIG. 6). The output of the source of direct current 32 is connected to the input of the voltage stabilizer 34 by an interface 36 formed for example as a plug. The voltage stabilizer 34 and the pulse generator 35 connected in series form a block of automatic contrast thermocycling which allows to cyclically reduce and increase the temperature of the heat contact plate 8 in a predetermined automatic mode. The block of automatic contrast thermocycling and the source of direct current 32 are preferably arranged in an additional casing (not shown in the drawings) with handles of a regulator of contrast thermocycling mode arranged on its front panel. The additional casing is fixed to the holder by thread-like elements (not shown in the drawings) which can be formed for example as wires connecting the massage blocks 1, 2 with the block of automatic contrast thermocycling.

The claimed device for local skin massage operates in the following manner. Depending on the size of the patient's head, the distance between the massage block 1, 2 is adjusted by changing the location of the end portion of the arcuate spring 23 in the curved slot 25, and simultaneously the force of pressing of the heat contact plates 8 to the skin is set. The location of the end portions of the arcuate springs 22, 23 in the slots 20 of the holders is adjusted, so as to adjust the location of the heat contact plates 8 with respect to the height, for example they are arranged in the temple area near the end of eyebrows. The regulators of the block of automatic contrast thermocycling (not shown in the drawings) set the predetermined parameters of the mode of contrast thermocycling: temperature of heating and cooling of the heat contact plates 8, the time of processes of heating and cooling, selected in accordance with the individual parameters of a patient. With the plug connection 36, the inlet of the voltage stabilizer 34 is connected to the outlet of the source of direct current 32. Direct current is supplied through the thermal elements of the massage blocks 1, 2 and due to Peltier effect the cooling of the heat contact plate 8 takes place (usually to 10°–17° C.). After elapsing of a predetermined time (for example during the time of pulse equal to 1 minute) the pulse generator 35 automatically switches the direction of current supplied through the thermal elements and performs heating of the heat contact plate 8 (usually heating is performed to 25°–32° C.). After elapsing of 1 minute, heating of the heat contact plate 8 is interrupted, the pulse generator 35 again automatically changes the direction of current supplied through the thermal elements, and the heat contact plate 8 is again cooled, etc.

The total time of the massaging session is usually 30–60 minutes. During the contrast thermocycling, periodic expansion (during heating) and contraction (during cooling) of the local skin portion located under the heat contact plate 8 occurs, and simultaneously with speed of exchange processes whereby a massage effect is achieved, and with sufficient number of massage sessions (usually 20–30) due to the stimulating action on the skin surface, gradual reduction of wrinkle depth on the skin is obtained up to its complete elimination. During the whole session the reliable heat contact of the heat contact plate 8 with the skin is maintained. After elapsing of the time provided for the massage session, the plug 36 disconnects the voltage stabilizer 34 from the source of direct current 32. For several minutes (usually 2–3 minutes), the device remains on the patient's head for gradual equalization of the temperature of the heat conduct plate 8 with the conventional skin temperature. The control of massage efficiency is performed by conventional methods used in industry. Test samples of the claimed device for local skin massage were produced by the applicant and successfully tested on tens of patient volunteers. When compared with known devices, the claimed device for local skin massage allows to considerably increase massage efficiency since it provides a carrying of the contrast thermocycling with uniform heat action on the portion to be massaged during the whole massage session. Without the use of surgical action, the "smoothing" of wrinkles on the face is performed, up to their complete disappearance. Simultaneously, the ergonomic properties is improved due to improvement of massage operator work conditions. In addition, the claimed device can be used not only in a beauty salon, but also in the household, for example in a passenger salon of a car, and even during working of a patient.

It will be understood that each of the elements described above, or two or more together, may also find a useful application in other types of constructions differing from the types described above.

While the invention has been illustrated and described as embodied in a device for local body massage, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of local skin massage comprising the steps of selecting a plurality of local skin portions for their subsequent temperature stimulation; placing each of heat contact plates of a plurality of massage thermoelectric blocks of a thermoelectric device above each of the plurality of the selected local skin portions; providing a fixed force of pressing the heat contact plates of the massage thermoelectric blocks against the plurality of the selected local skin portions; automatic performance of a temperature-time cycle including carrying out of sign-alternating processes of change of the electric currents simultaneously flowing through the thermal elements of the massage blocks operating on the base Peltier effect; and automatic uninterrupted successive repetition of the cycle with a predetermined frequency.

2. A method as defined in claim 1, wherein said sign-alternating process of changing direct electric current is performed so as to provide a predetermined contrast change of temperatures of cooling and heating of the heat contact plate within predetermined time and symbol-alternating ranges, but not exceeding ±25 ° relative to an initial temperature of a corresponding one of the local skin portions, said step of uninterrupted continuous repetition of the cycle being performed with a frequency provided by the thermoelectric device within provided in a region of infralow frequencies, but not less than $5.10^{-3}$ Hz.

3. A device for local skin massage, comprising a casing; heat contact plates arranged on said casing and placeable above a plurality of selected local skin portions; a commutating element arranged on said casing; means for cooling and heating of said heat contact plates including a source of direct current, thermal elements adjoining said heat contact plate, said commutating element connecting said source with said thermal elements; a system of heat withdrawal; a block of automatic contrast thermocycling for automatic performance of a temperature-time cycle including carrying out of sign-alternating processes of change of the electric currents simultaneously flowing through the thermal elements of the massage blocks operating on the base Peltier effect, and automatic uninterrupted successive repetition of the cycle with a predetermined frequency; a holder with a plurality of openings for a plurality of said casing; elements for pressing of said heat contact plate to a skin connected to said holder; said block of automatic contrast thermocycling being introduced between said source of direct current and said commutating element, each said opening of said holder having a spherical concave wall cooperating with a spherical convex surface in one of the casing and the system of heat withdrawal which forms with said opening a hinge connection, said holder being arranged so that it can move along said pressing elements.

4. A device as defined in claim 3, wherein said block of automatic contrast thermocycling includes a voltage stabilizer and a pulse generator connected in series so that an input of said voltage stabilizer is connected to an output of said source of direct current, and an output of said pulse generator is connected to said commutating element.

5. A device as defined in claim 3, wherein said system of heat withdrawal has said spherical convex surface which together with said spherical concave wall of said opening of said holder forms a hinge.

6. A device as defined in claim 3; and further comprising two identical massage blocks each including said heat contact plate arranged in said casing, said thermal elements adjoining said heat contact plate, said holder with said opening hingedly connected with said casing, and said system of heat withdrawal; and pressing elements connecting said massaging blocks with one another.

7. A device as defined in claim 6, wherein said pressing elements are formed as two parts connected with one another so as to change a relative position of said massage blocks.

8. A device as defined in claim 6, wherein said pressing elements are formed as a head of arcuate springs with end portions located in slots of said holders.

9. A device as defined in claim 8, wherein said head has a central zone provided with an arcuate fixator with a curved path, said arcuate spring has an end located in said slot.

10. A device as defined in claim 6, wherein said pressing elements are formed as curves of a spectacle frame which are connected by an arcuate spring, and a support element connected to a center of said spring, said massage blocks being arranged on said curves so as to move in two mutually perpendicular directions.

11. A device as defined in claim 6, wherein said pressing elements are formed as parts of a spectacle frame with each curve provided with a springy element such that each of said massage blocks is fixed on a respective one of said spring elements, said spring element being formed so that it is movable along said curve.

12. A method as defined in claim 3, wherein said spherical convex surface is formed in said casing.

13. A method for local skin massage, comprising a plurality of heat contact plates of plural massage thermoelectric blocks of a thermoelectric device, each thermoelectric block being placeable above each of a plurality of selected local skin portions; means for providing a fixed force of pressing the heat contact plates of the massage thermoelectric blocks against each of the plurality of the selected local skin portions; and means for automatic performance of a temperature-time cycle including carrying out of sign-alternating processes of change of the electric currents simultaneously flowing through the thermal elements of the massage blocks operating on the base Peltier effect, and for automatic uninterrupted successive repetition of the cycle with a predetermined frequency.

* * * * *